US006472196B1

(12) United States Patent
Fukuhara et al.

(10) Patent No.: US 6,472,196 B1
(45) Date of Patent: Oct. 29, 2002

(54) AMINO ACID SEQUENCE OF L-PHENYLALANINE AMMONIA-LYASE

(75) Inventors: Nobuhiro Fukuhara; Setsuo Yoshino; Kaoru Yamamoto, all of Yokohama; Tomoyuki Se, Zushi; Satori Sone, Yokohama; Yoshiyuki Nakajima, Yokohama; Maki Suzuki, Yokohama; Nobuyoshi Makiguchi, Fujisawa, all of (JP)

(73) Assignee: Mitsu Chemicals, Inc., Tokyo (JP)

( * ) Notice: Subject to any disclaimer, the term of this patent is extended or adjusted under 35 U.S.C. 154(b) by 0 days.

(21) Appl. No.: 08/214,018

(22) Filed: Mar. 15, 1994

Related U.S. Application Data

(60) Continuation of application No. 07/980,098, filed on Nov. 23, 1992, now abandoned, which is a continuation of application No. 07/740,855, filed on Jul. 31, 1991, now abandoned, which is a continuation of application No. 07/344,993, filed on Apr. 28, 1989, now abandoned, which is a division of application No. 07/095,464, filed on Sep. 11, 1987, now abandoned.

(30) Foreign Application Priority Data

Sep. 16, 1986 (JP) .......................................... 61-215864

(51) Int. Cl.[7] ................................................ C12N 9/88
(52) U.S. Cl. .................................... 435/232; 435/320.1
(58) Field of Search ................................ 435/91, 172.1, 435/172.3, 108, 252.33, 254.21, 320.1, 232; 536/23.1

(56) References Cited

PUBLICATIONS

Gilbert et al Journal of Bacteriol, vol. 161 1985. 314–320.*
Gilbert et al Journal of Bacteriol vol. 150 1982. 498–505.*
Hodgins Journal of Biol. Chem. vol. 246 (1971) 2977–2985.*

* cited by examiner

*Primary Examiner*—James Ketter
(74) *Attorney, Agent, or Firm*—Nixon & Vanderhye P.C.

(57) ABSTRACT

In order to provide technical information necessary for the production of L-phenylalanine ammonia-lyase (PAL) by utilizing genetic engineering techniques, the structural gene for PAL and the amino acid sequence of PAL have been elucidated in *Rhodosporidium toruloides*, and novel recombinant DNA plasmids (e.g., pSW101, pYtrp6 and pKY201) have been created by inserting a DNA strand coding for the PAL gene between the 3'-terminus of the promoter region and the 5'-terminus of the terminator region.

Moreover, transformants having such a novel recombinant DNA plasmid have been created, and a process for the production of PAL by growing such a novel transformant so as to cause PAL to be produced and accumulated in the culture has been established.

Furthermore, there has been established a novel technique for the production of L-phenylalanine by reacting an ammonia donor with cinnamic acid in the presence of the PAL prepared by the aforesaid novel process.

4 Claims, 6 Drawing Sheets

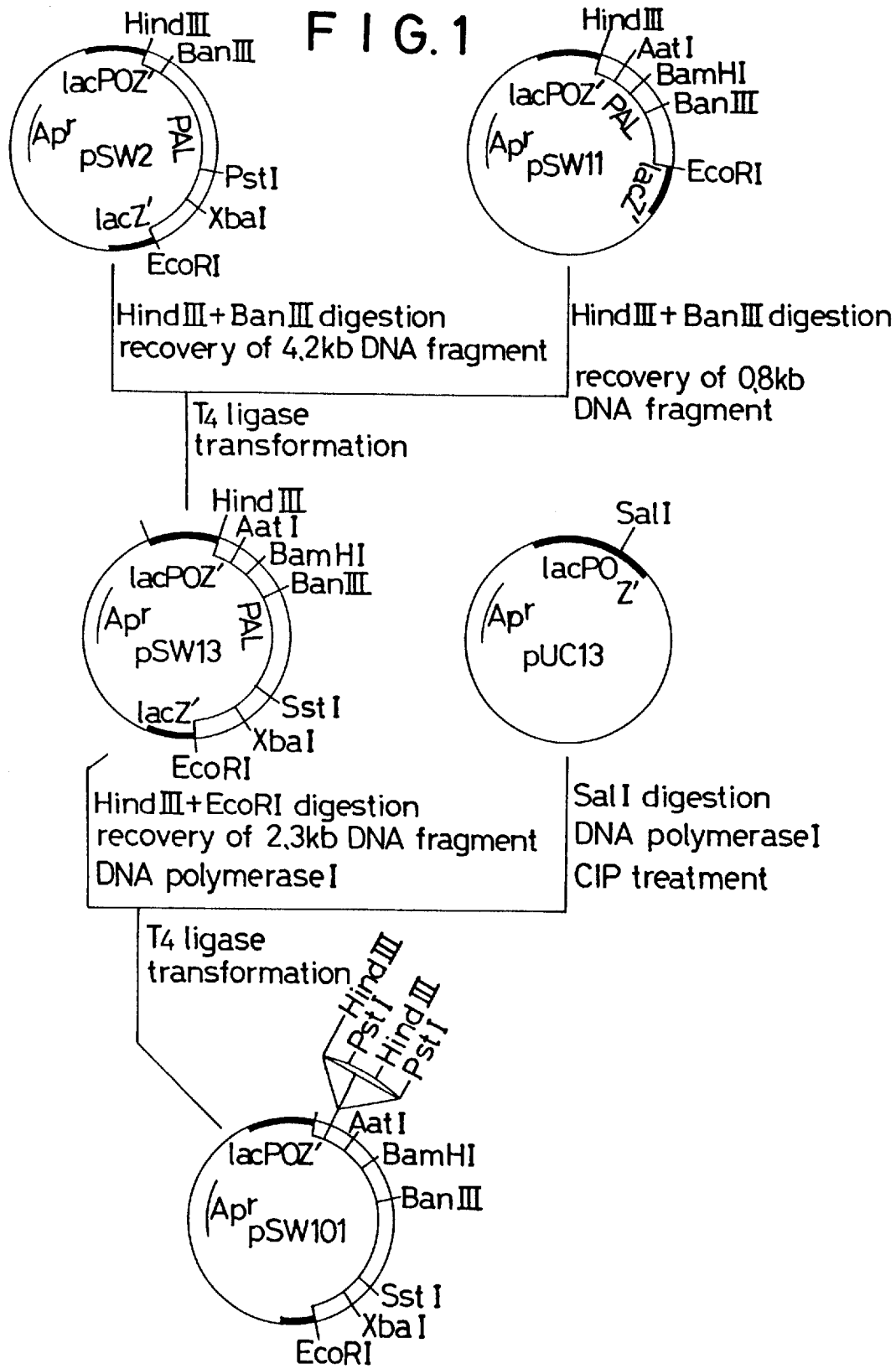
F I G. 1

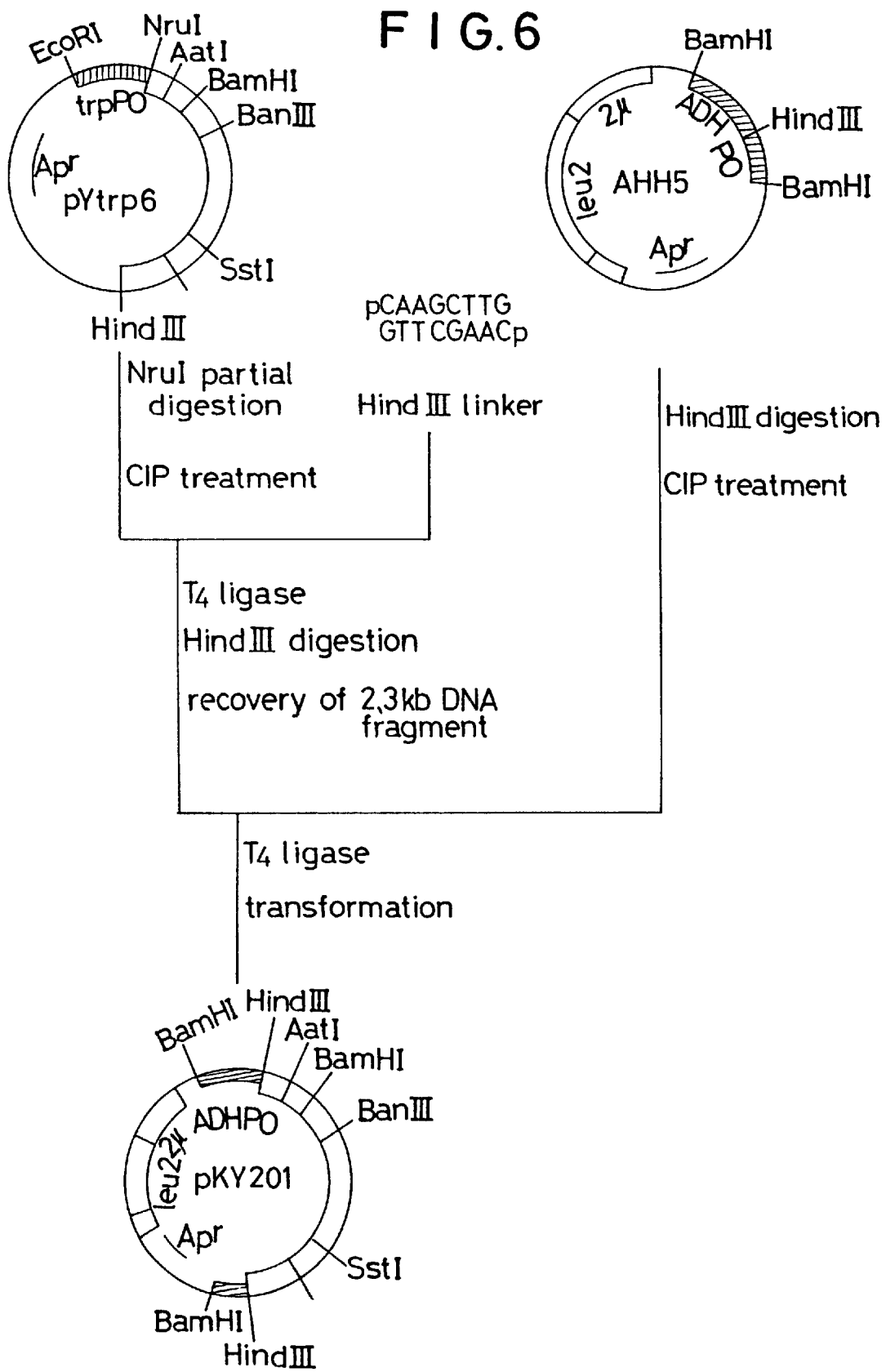

AMINO ACID SEQUENCE OF L-PHENYLALANINE AMMONIA-LYASE

This is a continuation of application Ser. No. 07/980,098, filed Nov. 23, 1992, which is a continuation of 07/740,855, filed Jul. 31, 1991, which is a continuation of 07/344,933, filed Apr. 28, 1989, which is a division of 07/095,464, filed Sep. 11, 1987, all now abandoned.

BACKGROUND OF THE INVENTION

1. Field of the Invention

This invention relates to L-phenylalanine ammonia-lyase (hereinafter abbreviated as PAL) having a novel amino acid sequence and useful in the production of L-phenylalanine (sometimes abbreviated as L-Phe).

This invention also relates to the structural gene for PAL (sometimes also referred to as PAL gene) derived from *Rhodosporidium toruloides*, DNA sequences comprising the structural gene for PAL having joined thereto one or more necessary elements which permit the gene to be expressed in other prokaryotic or eukaryotic host microorganisms, and recombinant DNA plasmids for the expression of PAL containing such a DNA sequence.

This invention further relates to microorganisms transformed with such a recombinant DNA plasmid for the expression of PAL, a process for the production of PAL by using such a transformant, the PAL produced by such a transformant, and a process for the production of L-Phe by using the PAL so prepared.

2. Description of the Prior Art

L-Phe is one of the essential amino acids. It is an aromatic amino acid that is not only necessary for nutrition but also useful as the raw material for the manufacture of Aspartame recently in use as an artificial sweetener.

It is known that PALs derived from *Rhodosporidium toruloides* and other microorganisms of the genus Rhodotorula can be utilized for the production of L-Phe.

Processes for the production of PAL are disclosed, for example, in Japanese Patent Publication No. 10753/'69 and Japanese Patent Laid-Open No. 86082/'83.

In addition, Japanese Patent Publication No. 10753/'69 also teaches a method for inducing the production of the enzyme by contacting a microorganism of the genus Rhodotorula with L-phenylalanine, and Japanese Patent Laid-Open No. 86082/'83 also teaches a method for inducing the production of the enzyme by contacting a microorganism of the genus Rhodotorula with an amino acid such as L-isoleucine, L-valine, L-leucine or the like.

In the prior art including the aforesaid processes and methods, the production of PAL requires the step of bringing an amino acid suitable for the induction of PAL production into contact with a microorganism having the ability to produce PAL.

However, the industrial production of PAL by using the aforesaid processes and methods is disadvantageous from an economic or technical point of view, because an expensive amino acid must be used in large amounts, cultivation of the microorganism cannot be managed easily, and a satisfactorily high induction-efficiency cannot always be achieved.

Meanwhile, recent progress in molecular biology has made it possible to isolate a DNA strand coding for a protein originating from a certain microorganism and transform a microorganism of different species by introducing the DNA strand thereinto.

By utilizing such genetic engineering techniques, it may be expected that the necessity of inducing PAL production by contacting an expensive amino acid with a microorganism having the ability to produce PAL is eliminated and, therefore, cultivation of the microorganism can be managed easily.

However, no report has yet been published on the analysis of the structural gene for PAL, isolation and cloning thereof, and the amino acid sequence of PAL. Thus, the technical information necessary for the production of PAL by utilizing genetic engineering techniques has not been available in the existing state of the art.

SUMMARY OF THE INVENTION

The present invention has been made in view of the above-described existing state of the art concerning the production of PAL.

It is an object of the present invention to provide a novel structural gene for PAL which is useful in the production of PAL by utilizing genetic engineering techniques, a recombinant plasmid for the expression of PAL containing the gene, and a transformant having the recombinant plasmid.

It is another object of the present invention to provide a process for the production of PAL in which PAL can be efficiently produced at low cost, cultivation of the microorganism can be managed easily, and the production of PAL can be carried out on an industrial scale.

It is still another object of the present invention to provide PAL having a novel amino acid sequence and useful for the production of L-Phe, and a process for the production of L-Phe by using the PAL.

In order to accomplish these objects, the present inventors have made intensive studies and have achieved the following results:

(1) It has been made clear that PAL derived from *Rhodosporidium toruloides* has an amino acid sequence which will be shown later.

(2) Novel recombinant DNA plasmids (e.g., pSW101, pYtrp6 and pKY201) have been created by inserting a DNA strand coding for the PAL gene between the 3'-terminus of the promoter region and the 5'-terminus of the terminator region.

(3) Transformants having such a novel recombinant DNA plasmid [i.e., *Escherichia coli* MT-10410 (FERM BR1710) and MT-10414 (FERM BR1712), and bakers' yeast MT-40390 (FERM P-8875)] have been created.

(4) There has been established a novel process for the production of PAL by growing such a novel transformant so as to cause PAL to be produced and accumulated in the culture.

(5) There has been established a novel technique for the production of L-phenylalanine by reacting an ammonia donor with cinnamic acid in the presence of the PAL produced by the aforesaid novel process and having a novel amino acid sequence.

The present invention, which includes the new findings and techniques described in the above Paragraphs 1 to 5, has made it possible to produce PAL efficiently at low cost in a simplified cultivation process utilizing genetic engineering techniques.

More specifically, according to the present invention, a microorganism easy of mass cultivation can be transformed with a recombinant plasmid for the expression of PAL, and the resulting transformant can be easily cultivated to produce PAL. Moreover, this cultivation process does not require any highly elaborate techniques or any expensive induction reagents. Thus, the production of PAL in accordance with the present invention does not require any conventional hard-to-manage cultivation process including the step of including PAL by contacting an expensive amino acid with a microorganism having the ability to produce PAL.

Moreover, the PAL produced by the microorganism obtained in accordance with the present invention is stable and suitable for use in the industrial production of L-phenylalanine. Furthermore, the present invention has the additional advantage that, where the PAL is expressed in *Escherichia coli* or the like, there is no need for contacting the microorganisms with a surface active agent to enhance the permeability of the cell wall.

BRIEF DESCRIPTION OF THE DRAWINGS

FIG. 1 is a flow chart illustrating the procedure for the construction of pSW101;

FIG. 6 is a flow chart for the construction of pKY201.

DETAILED DESCRIPTION OF THE INVENTION

Figure 2:
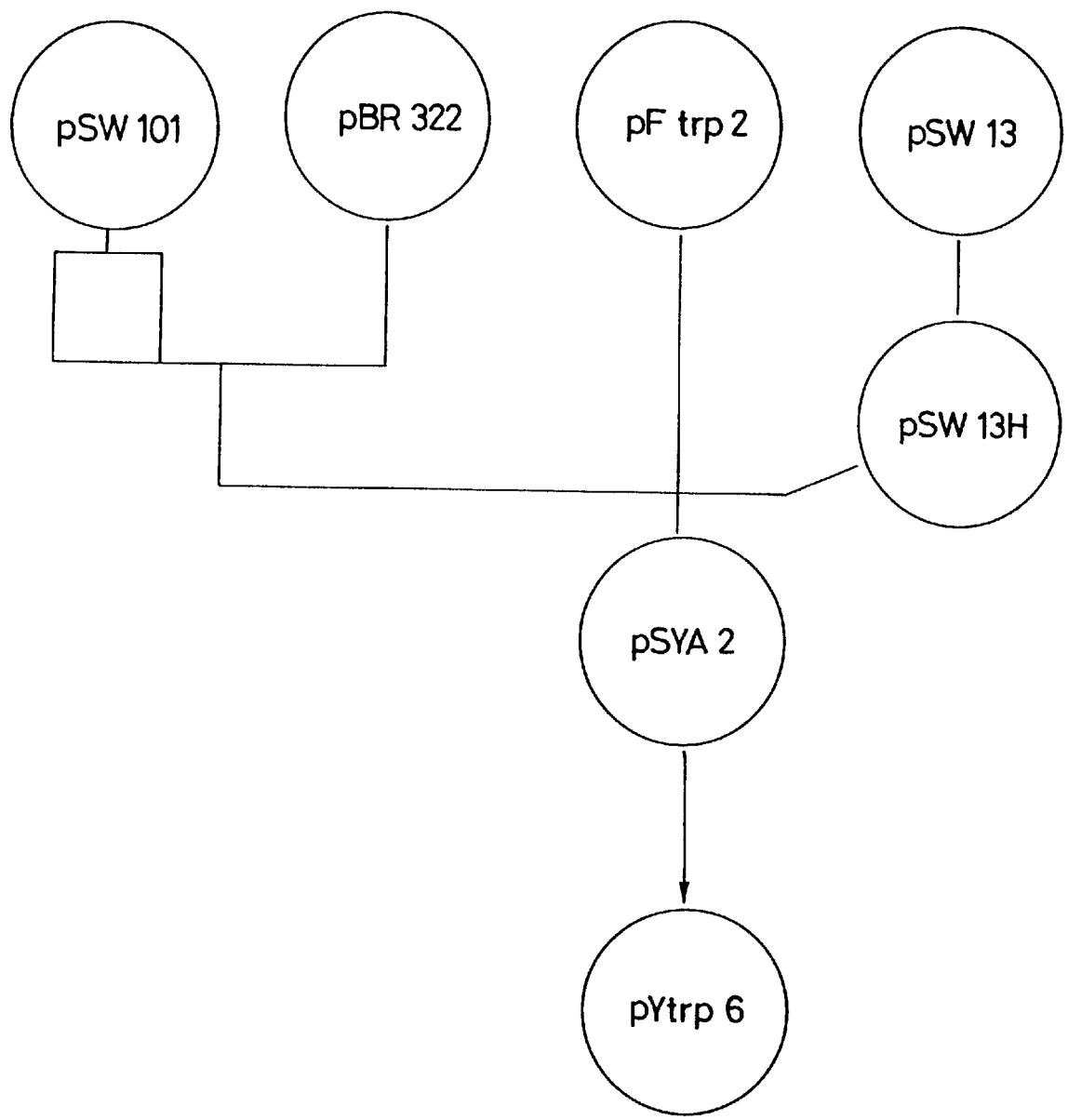
FIG. 2 is a flow chart for the construction of pYtrp6.

The structural gene for PAL of the present invention can be obtained by carrying out a series of steps, which include the following most essential ones:

(1) Isolation and purification of the messenger RNA (mRNA) for PAL.
(2) Conversion of the mRNA into double-stranded DNA (ds-cDNA).
(3) Construction of ds-cDNA having an oligo-dC tail added thereto.
(4) Construction of a hybrid plasmid by joining the oligo-dC tailed ds-cDNA to a vector having an oligo-dG tail added thereto.
(5) Transformation of a microorganism and selection of clones.
(6) Confirmation of the characters of the PAL gene region by analysis of the DNA sequence.
(7) Confirmation of the expression of PAL enzyme activity.

The structural gene for PAL can be incorporated into vectors capable of replicating in various hosts (such as *Escherichia coli, Bacillus subtilis*, bakers' yeast, etc.), by inserting it between the 3'-terminus of the promoter region functioning in the respective hosts and the 5'-terminus of the terminator region. Thus, there can be constructed recombinant DNA plasmids permitting the expression of PAL.

The promoter region used for this purpose can be any region that contains a site at which RNA polymerase can bind to initiate the synthesis of mRNA.

This promoter region additionally contains a translation initiation region. For example, where the host is *E. coli*, the translation initiation region extends from the Shine-Dalgarno sequence or the ribosome binding site (i.e., the site corresponding to the nucleotide sequence of mRNA to which a ribosome can bind) to the initiator codon (e.g., ATG). Preferably, the distance between the Shine-Dargarno sequence and the initiator codon is about 10 bases long.

Where the host is a procaryote such as *E. coli*, the terminator region is not always necessary. However, the presence of a terminator region is known to have some additional effects.

Accordingly, where *E. coli* is used as the host, the structural gene for PAL may be inserted into a plasmid capable of replicating in *E. coli*, at the 3'-terminus of the promoter region present in the plasmid and functioning in *E. coli*.

Preferred promoter regions include, for example, the tryptophan (trp) promoter, the lactose (lac) promoter, the tac promoter, the PL lambda promoter and the like. Thus, various vectors (such as pBR322, pUC and the like) containing these promoter regions are useful in the present invention.

In practice, such a vector is cleaved with a suitable restriction endonuclease at the 3'-terminus of the promoter region. If the structural gene for PAL has the same cohesive ends, it can be directly inserted into the vector. If the cohesive ends of the PAL gene have unmatched DNA sequences, flush ends are generated. Then, the PAL gene can be inserted into the vector by means of a ligase.

In this connection, more detailed information may be found in the References that will be collectively given later. Specifically, the tryptophan promoter is described in References 1 to 4, the lactose promoter in Reference 5, the tac promoter in Reference 6, the PL lambda promoter in References 7 and 8, and the terminator region in Reference 9.

A recombinant DNA plasmid constructed by inserting the PAL gene between the 3'-terminus of the promoter region and the 5'-terminus of the terminator region can be used to transform *E. coli* according to the well-known method.

The resulting transformants can be selected on the basis of a phenotypic character such as drug resistance (e.g., resistance to ampicillin), auxotrophy or the like. Then, cells having PAL activity are selected from the cells exhibiting such a phenotypic character.

A transformant selected in the above-described manner can be grown in the well-known manner. The medium used for this purpose can be, for example, a broth or a synthetic medium containing glucose and/or other required nutrient(s).

If it is desired to cause the promoter to function more efficiently, a chemical agent such as isopropyl-β-thiogalactoside (hereinafter abbreviated as IPTG) or indoleacrylic acid (hereinafter abbreviated as IAA) may be added to the medium.

The transformant is usually incubated at a temperature of 15 to 43° C., preferably 28 to 42° C., for a period of 4 to 48 hours, preferably 4 to 20 hours. If necessary, aeration and/or agitation may be employed.

Where bakers' yeast (*Saccharomyces cerevisiae*) is used as the host, its transformants can be created in the following manner:

Into an *E. coli*-yeast shuttle vector, such as YRp7 (its method of preparation is described in Reference 10) or pMA3a (its method of preparation is described in Reference 11), is inserted a promoter region functioning in bakers' yeast, such as the promoter region of the glyceraldehyde-3-phosphate dehydrogenase gene (its method of preparation is described in Reference 12) or the promoter region of the alcohol dehydrogenase I gene (its method of preparation is described in Reference 13). Then, a DNA fragment containing the structural gene for PAL is joined to the 3'-terminus of the inserted promoter region by means of a ligase. Further, the 3'-terminal untranslated region, which is not translated by mRNA and which is included in the alcohol dehydrogenase I gene, or the 3'-terminal untranslated region which is not translated by mRNA and which is included in the glyceraldehyde-3-phosphate dehydrogenase gene as a terminator is selected and joined to the 3'-terminus of the structural gene for PAL by means of a ligase. Thereafter, the plasmid is cyclized by joining the 3'-terminus of the selected untranslated region to the 5'-terminus of the shuttle vector.

Using this cyclized plasmid, *E. coli* is transformed according to the well-known method.

The resulting transformants can be selected on the basis of a phenotypic character such as resistance to ampicillin.

From the cells of these *E. coli* transformants, plasmid DNA is isolated according to the alkali extraction method. Using this plasmid, an auxotrophic strain of yeast [such as MT-40391 lysine-dependent strain obtained by mutation of *S. cerevisiae* ATCC 44771 strain] is transformed according to the well-known or other equivalent method.

The transformed yeast can be selected on the basis of reversion of the auxotrophy of the host.

The transformed yeast can be grown in any of various well-known media. The medium used for this purpose can be, for example, a medium prepared by adding glucose and other required nutrient(s) to Wickerham's amino acid-free medium (Reference 14).

The yeast is usually incubated at a temperature of 15 to 40° C. for a period of 24 to 72 hours. If necessary, aeration and/or agitation may be employed.

After the microorganism is grown in the above-described manner, the cells can be collected from the resulting culture according to any conventional procedure, and the PAL produced and accumulated in the collected cells can be extracted by destroying their cell wall and other cellular structures. To this end, there may be employed contact with an organic solvent, a surface active agent or the like; mechanical treatments such as sonication, glass bead disintegration and the like; and biochemical procedures such as treatment with-a suitable lytic enzyme, autolysis and the like.

The crude enzyme prepared in the above-described manner, the immobilized cells obtained by embedding the collected cells in an immobilizing agent such as polyacrylamide gel or arginate gel, or the collected cells thereselves may be used to effect the enzymatic reaction of an ammonia donor with cinnamic acid and thereby produce L-Phe. This enzymatic reaction can be carried out according to various conventional processes including, for example, the process of Japanese Patent Publication No. 44474/'86 in which the reaction mixture contains an ammonia donor in large excess relative to cinnamic acid and the concentration of cinnamic acid does not exceed the inhibitory level for the enzymatic reaction.

The present invention is more specifically explained in stages with reference to the following example.

EXAMPLE

1. Isolation and Purification of the mRNA for PAL

Using a synthetic medium (Table 1) containing 2% glucose, Rhodosporidium toruloides IFO 559 (also identified as ATCC 10788) was grown at 27° C. under aerated and agitated conditions. Immediately after all of the glucose added at the beginning of the culture was consumed, the bacterial cells were collected by centrifugation. The collected wet cells were washed with 0.85% sterile saline and collected again by centrifugation to obtain wet washed cells.

TABLE 1

| Glucose | 20 g/l | Biotin | 2 µg/l |
|---|---|---|---|
| $(NH_4)_2SO_4$ | 3 " | Calcium pantothenate | 400 |
| $KH_2PO_4$ | 1 " | Inositol | 2000 |
| $MgSO_4 \cdot 7H_2O$ | 0.5 " | Niacin | 400 |
| NaCl | 0.1 " | p-Aminobenzoic acid | 200 |
| $CaCl_2$ | 0.1 " | Pyridoxine hydrochloride | 400 |
| | | Riboflavin | 200 |
| | | Thiamine hydrochloride | 400 |

The wet washed cells were immediately suspended in a PAL induction medium [i.e., 0.17% Yeast Nitrogen Base (a product of Difco; ammonium sulfate-free and amino acid-free type) containing 2% L-Phe] to a cell concentration of 0.5–0.8%, and the resulting suspension was shaken at 27° C. to induce PAL.

After 2 hours' treatment for induction of PAL at 27° C., the cells were recovered from the PAL induction medium by centrifugation. The collected wet cells were suspended in an equal volume of sterile water, and the resulting suspension was dropped into liquid nitrogen to obtain frozen cells.

The frozen cells (10 g) were added to liquid nitrogen in a mortar and finely ground with a pestle. Then, as soon as the liquid nitrogen evaporated spontaneously and the ground frozen material began to thaw, 50 ml of a buffer solution C [composed of 0.1M $Na_2HPO_4$ (pH 7.4), 0.15M sodium chloride, 1% sodium deoxycholate and 1% Triton X-100] containing 5% SDS was added thereto and gently stirred for 30 minutes.

After completion of the stirring, 50 ml of a phenol-chloroform mixture (composed of phenol, chloroform and isoamyl alcohol in a volume ratio of 25:24:1) was added thereto and mixed therewith by stirring for 15 minutes.

The resulting mixture was centrifuged and the aqueous phase was recovered. To this aqueous phase was added 50 ml of fresh phenol-chloroform mixture, followed by stirring for 15 minutes. After centrifugation, the aqueous phase was recovered again. Subsequently, this procedure for extraction with the phenol-chloroform mixture was repeated twice more.

To the finally obtained aqueous phase was added 5M sterile saline so as to give a final sodium chloride concentration of 0.2M. Then, 2.5 volumes of cold ethanol was added thereto. The resulting mixture was stored at −20° C. or below to precipitate the nucleic acid components.

The precipitate so formed was collected by centrifugation, washed with cold ethanol, and then dried under reduced pressure.

The dry material thus obtained was dissolved in 10 ml of sterile water, and the resulting solution was heat-treated at 65° C. for 5 minutes. Thereafter, mRNA was isolated according to the well-known method of Maniatis (Reference 15) using oligo-d(T) cellulose.

The mRNA thus obtained was dissolved in a sample buffer solution (composed of 5M urea, 1 mM EDTA and 0.05% Bromophenol Blue) and then heat-treated at 65° C. for 2 minutes to destroy its higher-order structure. Thereafter, using an 8M urea-acrylamide slab gel (having an acrylamide concentration of 3% and containing 8M urea), the mRNA was subjected to electrophoresis in an electrophoretic buffer solution (composed of 89 mM Tris, 89 mM boric acid and 2 mM EDTA).

After completion of the electrophoresis, the acrylamide gel was treated with ethidium bromide and mRNA bands were visualized under ultraviolet light. The gel portion corresponding to an mRNA size range of 2.0 to 3.0 kb was divided into three equal parts in the lengthwise direction, and three gel segments were cut out of the slab gel.

Each gel segment was sealed in a dialysis tube, which was immersed in an electrophoretic buffer solution having the aforesaid composition. Thus, the mRNA was electrically eluted from the gel segment.

To the liquid inside each dialysis tube was added a phenol-chloroform mixture. The resulting mixture was extracted twice with water and the aqueous phase thus obtained was further extracted with ether to remove any residual phenol. To this aqueous phase were added 1/10 volume of a 3M aqueous solution of sodium acetate (pH 5.2) and then 2.5 volumes of cold ethanol. The resulting mixture was stored at −20° C. to precipitate the mRNA.

In order to determine whether the mRNA fraction purified from each gel segment contained the mRNA for PAL or not, the mRNA contained in each fraction was translated into proteins and the produced proteins were tested with an antibody specific for PAL.

More specifically, each mRNA fraction was subjected to experiments with a cell-free translation kit using the lysate of rabbit reticulocytes (Reference 16).

The rabbit reticulocyte assay kit used was a product of Promega Biotec Co. and the labeled amino acid used was $^{35}$S-methionine (a product of Amersham Co.).

The PAL included in the proteins synthesized in the in vitro translation system using rabbit reticulocytes was identified as follows: To the translation mixture was added buffer solution C in order to dissolve the proteins. After the insoluble matter was removed by centrifugation, self-prepared anti-PAL rabbit IgG was added to the supernatant and this reaction mixture was allowed to stand on ice for 30 minutes. Then, anti-rabbit IgG goat serum (self-prepared) was added to the reaction mixture, followed by standing on ice for 30 minutes. Thus, proteins were precipitated together with the rabbit antibody.

The precipitate was recovered by centrifugation, washed twice with buffer solution C, and then dissolved in a solution formed by mixing a mixture of 2% SDS and 10% β-mercaptoethanol solution with a mixture of 0.1 M Tris-phosphate (pH 6.8), 1% SDS and 50% glycerol solution in a volume ratio of 3:1. This reaction mixture was heated at 95° C. for 2 hours to sever the disulfide linkages of the proteins. Then, the reaction mixture was subjected to SDS-polyacrylamide slab gel electrophoresis (at an acrylamide concentration of 10%) according to Laemnli's method (Reference 17). After completion of the electrophoresis, the gel was dried and PAL was detected by autoradiography. Thus, the fraction containing the mRNA for PAL was determined.

2. Conversion of the mRNA for PAL to Double-stranded cDNA (ds-cDNA)

The fraction from the gel segment containing the mRNA for PAL, which had been obtained from the cells subjected to 2 hours' treatment for the induction of PAL as described in Section 1 above, was purified. Then, according to the procedure described in Reference 18, the mRNA thus obtained was treated with Awv reverse transcriptase to convert it to a single-stranded cDNA. molecule.

More specifically, a single-stranded cDNA-mRNA hybrid was formed and then treated with RNaseH, DNA polymerase I and a ligase. Thus, the mRNA was removed and, at the same time, double-stranded cDNA (ds-cDNA) was constructed.

3. Construction of ds-cDNA having an Oligo-dC Tail Added to its 3'-terminus

The ds-cDNA obtained in Section 2 above was treated with terminal deoxynucleotidyl transferase (TdT) to add an oligo-dC tail to the 3'-terminus of the ds-cDNA.

More specifically, 3 μg of the ds-cDNA was dissolved in a reaction medium containing a TdT buffer solution [composed of 100 mM potassium cacodylate (pH 7.2), 2 mM cobalt chloride and 0.2 mM dithiothreitol] and 0.2 mM dCTP, and pretreated at 37° C. for 5 minutes. Then, 50 units of TdT was added and the resulting reaction mixture was incubated at 37° C. for 15 minutes so as to allow the reaction to proceed. Thereafter, EDTA was added to a final concentration of 40 mM and the reaction mixture was placed on ice. Then, TdT was denatured and inactivated by the addition of a phenol-chloroform mixture. After the denatured insoluble protein was removed from the reaction mixture by centrifugation, the supernatant was extracted with phenol and the separated aqueous phase was mixed cold ethanol. The precipitate so formed was collected, washed with 70% ethanol, and then dried under reduced pressure to obtain ds-cDNA having an oligo-dC tail added to its 3'-terminus.

4. Construction of a Hybrid Plasmid
[Joining of a pUC9 Molecule (having an Oligo-dG Tail) to a ds-cDNA Molecule (having an Oligo-dC Tail)]

The oligo-dC tailed ds-cDNA obtained in Section 3 above was joined to the plasmid pUC9 (having an oligo-dG tail; readily available from Pharmacia Co., Sweden) according to Maniatis' method that is known as the dC-dG homopolymer method.

5. Transformation and Selection of Clones

The hybrid plasmid obtained in Section 4 above (consisting of an oligo-dG tailed pUC9 molecule and an oligo-dC tailed ds-cDNA molecule) was introduced into $CaCl_2$-treated cells of E. coli MC 1061 (Reference 26) according to the competent cell method.

After about 40,000 transformant colonies were obtained, the selection of transformed cells were carried out according to a colony hybridization process based on the procedure described in Reference Example 3 that will be given later.

From the positive colonies thus obtained, plasmids were extracted and purified. These plasmids were cleaved with various restriction endonucleases, and the sizes of the resulting DNA fragments were analyzed by agarose gel electrophoresis.

6. Construction of ds-cDNA Containing the Complete Structural Gene for PAL

Plasmids pSW2 and pSW11 were isolated from the transformants obtained in Section 5 above.

Moreover, as a result of the analysis carried out in Section 5 above by using various restriction endonucleases, it was found that the complete cDNA corresponding to the mRNA for PAL could be constructed by combining pSW2 with pSW11. Thus, these plasmids were extracted and purified from transformed cells containing them.

The plasmids obtained from cells containing pSW2 were cleaved with the restriction endonuclease BanIII, and then with the restriction endonuclease HindIII. The resulting fragment mixture was fractionated by agarose gel electrophoresis. Thus, a DNA fragment having a size of 4.2 kb was recovered and purified by subjecting it several times to a procedure comprising treatment with a phenol-chloroform mixture and precipitation with cold ethanol.

On the other hand, the plasmids obtained from cells containing pSW11 were cleaved with the restriction endonucleases BanIII and HindIII. By subjecting the resulting fragment mixture to electrophoresis, a DNA fragment having a size of 0.8 kb was recovered and purified.

These 4.2 kb and 0.8 kb DNA fragments were cyclized with a ligase, and the resulting product was used to transform E. coli JM83 (ATCC 35607, Reference 27).

Plasmids were extracted from the transformants exhibiting ampicillin resistance used as the marker, and then treated with various restriction endonucleases to construct cleavage maps. Thus, a plasmid pSW13 having the correct PAL structure shown in the restriction endonuclease cleavage map of FIG. 1 was selected.

7. Determination of Nucleotide Sequence of Cloned DNA

The aforesaid plasmid pSW13 was isolated from clones containing it, and this cloned DNA fragment was cleaved with various restriction endonucleases. With suitable restriction fragments, their nucleotide sequences were analyzed by Maxam-Gilbert's method (chemical decomposition method), and also biochemically by Maat's dideoxy method (Reference 19).

The resulting nucleotide sequences of the respective DNA fragments were edited by computer processing. The nucleotide sequence so determined was identical to the nucleotide sequence of cDNA containing the structural gene for PAL which will be shown later.

8. Construction of pSW101 (See FIG. 1)

In 14 $\mu$l of a reaction medium [composed of 7 mM Tris-HCl (pH 7.5), 0.7 mM EDTA, 7 mM $MgCl_2$, 175 mM NaCl, 7 mM β-mercaptoethanol and 0.01% bovine serum albumin (hereinafter abbreviated as BSA)], 0.9 $\mu$g of the plasmid pUC13 (a product of Pharmacia Co.) was treated with 10 units of the restriction endonuclease SalI at 37° C. for 16 hours. Subsequent treatment with a phenol-chloroform mixture and precipitation with ethanol gave linear DNA. Then, in a nick translation buffer solution [composed of 50 mM Tris-HCl, (pH 7.5), 10 mM $MgCl_2$, 0.1 mM dithiothreitol, 2% BSA, 80 $\mu$M DATP, 80 $\mu$M dGTP, 80 $\mu$M dTTP and 80 $\mu$M dCTP], this linear DNA was treated with the Klenow fragment of DNA polymerase (a product of Takara Shuzo K.K.) at room temperature for 30 minutes. Thus, its cohesive ends were converted to flush ends. After deproteinization with phenol, DNA was precipitated with cold ethanol and recovered. By treating this DNA fragment with a phosphodiesterase derived from calf spleen (CIP; a product of Böhringer Co.), the 5'-terminal phosphoryl groups were removed to prevent self-cyclization of the linear pUC13.

On the other hand, the plasmid pSW13 was extracted and purified from cells containing it. In a reaction medium [composed of 4 mM Tris-HCl (pH 7.5), 0.4 mM EDTA and 50 mM NaCl], the plasmid pSW13 was treated with the restriction endonuclease DraI at 37° C. for 28 hours. Then, after saline was added thereto so as to give a sodium chloride concentration of 100 mM, the plasmid pSW13 was further treated with the restriction endonucleases EcoRI and HindIII at 37° C. for 16 hours.

After completion of the treatment, the reaction mixture was subjected to agarose gel electrophoresis, and a DNA fragment having a size of 2.3 kb was recovered from the gel. Then, this DNA fragment was subjected three times to a procedure comprising extraction with phenol, treatment with a phenol-chloroform mixture, and precipitation with cold ethanol. Thus, there was obtained a cDNA fragment coding for PAL.

In the aforesaid nick translation buffer solution, the cDNA fragment was treated with the Klenow fragment of DNA polymerase at room temperature for 45 minutes, and then subjected three times to a procedure comprising treatment with a phenol-chloroform mixture and precipitation with cold ethanol. Thus, there was obtained a cDNA fragment having flush ends.

Then, a circular plasmid pSW101 was constructed by joining the flush-ended pUC13 fragment to the flush-ended cDNA fragment by means of a ligase.

Using this hybrid DNA plasmid, E. coli JM83 was transformed according to the well-known method. A cell strain (MT-10410, FERM BP-1710) was selected from among ampicillin-resistant colonies, and its PAL activity was determined.

9. Construction of pYtrp6 and Transformation

The plasmid pSW101 constructed in the manner described in Section 8 above was digested with PstI and BamHI. After the resulting fragment mixture was subjected to agarose gel electrophoresis, DNA fragments of 370 bp were recovered. These fragments were divided into two parts, and one of them was digested with BanI and the other with BbeI.

After digestion, the resulting fragment mixture was subjected to acrylamide gel electrophoresis. Thus, a fragment having a size of 70 bp was recovered from the BanI digest and a fragment having a size of 280 bp was recovered from the BbeI digest.

The 70 bp fragment was treated with DNA polymerase to generate flush ends, to which ClaI(BanIII) linkers were joined by means of a ligase.

This DNA fragment having ClaI linkers joined to its both ends was digested with BanIII and BbeI. On the other hand, pBR322 was digested with BanIII and BamHI, and a DNA fragment of 4.0 kb was recovered by agarose gel electrophoresis. The aforesaid BanIII+BbeI fragment and the previously prepared BbeI fragment (280 bp) were joined to the pBR322 fragment (4.0 kb) by means of a ligase. Thus, there was obtained a plasmid pSYA1. Then, E. coli was transformed with pSYA1 according to the well-known calcium method.

E. coli containing pSYA1 was inoculated into 3 ml of LB medium containing ampicillin and incubated at 37° C. overnight. The grown cells were collected by centrifugation and suspended in 60 $\mu$l of a solution composed of 50 mM glucose, 25 mM Tris-HCl (pH 8.0) and 10 mM EDTA to form a cell suspension. Then, 40 $\mu$l of a 10 mg/ml lysozyme solution was added thereto and the resulting reaction mixture was allowed to stand at room temperature for 5 minutes. After completion of the reaction, 200 $\mu$l of 0.2N NaOH containing 1% SDS was added thereto. After gentle vortexing, the reaction mixture was placed on ice and allowed to stand for 5 minutes. Then, 150 $\mu$l of a 5M sodium acetate solution (pH 4.8) was added thereto. After gentle vortexing, the reaction mixture was placed on ice to stop the reaction.

The resulting lysate was centrifuged at 12,000 rpm for 10 minutes and the supernatant was separated. Then, this supernatant was subjected three times to a procedure comprising treatment with a phenol-chloroform mixture and precipitation with cold ethanol.

From the precipitate thus obtained, pSYA1 was extracted according to conventional procedure. After pSYA1 was digested with BamHI and BanIII, a DNA fragment having a size of 350 kb was recovered.

On the other hand, the plasmid pSW13 constructed in Section 6 above was digested with XbaI and the resulting cohesive ends were treated with DNA polymerase to generate flush ends. Then, a HindIII linker was joined thereto by means of a ligase to construct pSW13H. The pSW13H thus obtained was digested with BamHI and HindIII. From the resulting digest, a DNA fragment having a size of 1.9 kb was recovered by agarose gel electrophoresis.

Figure 4:
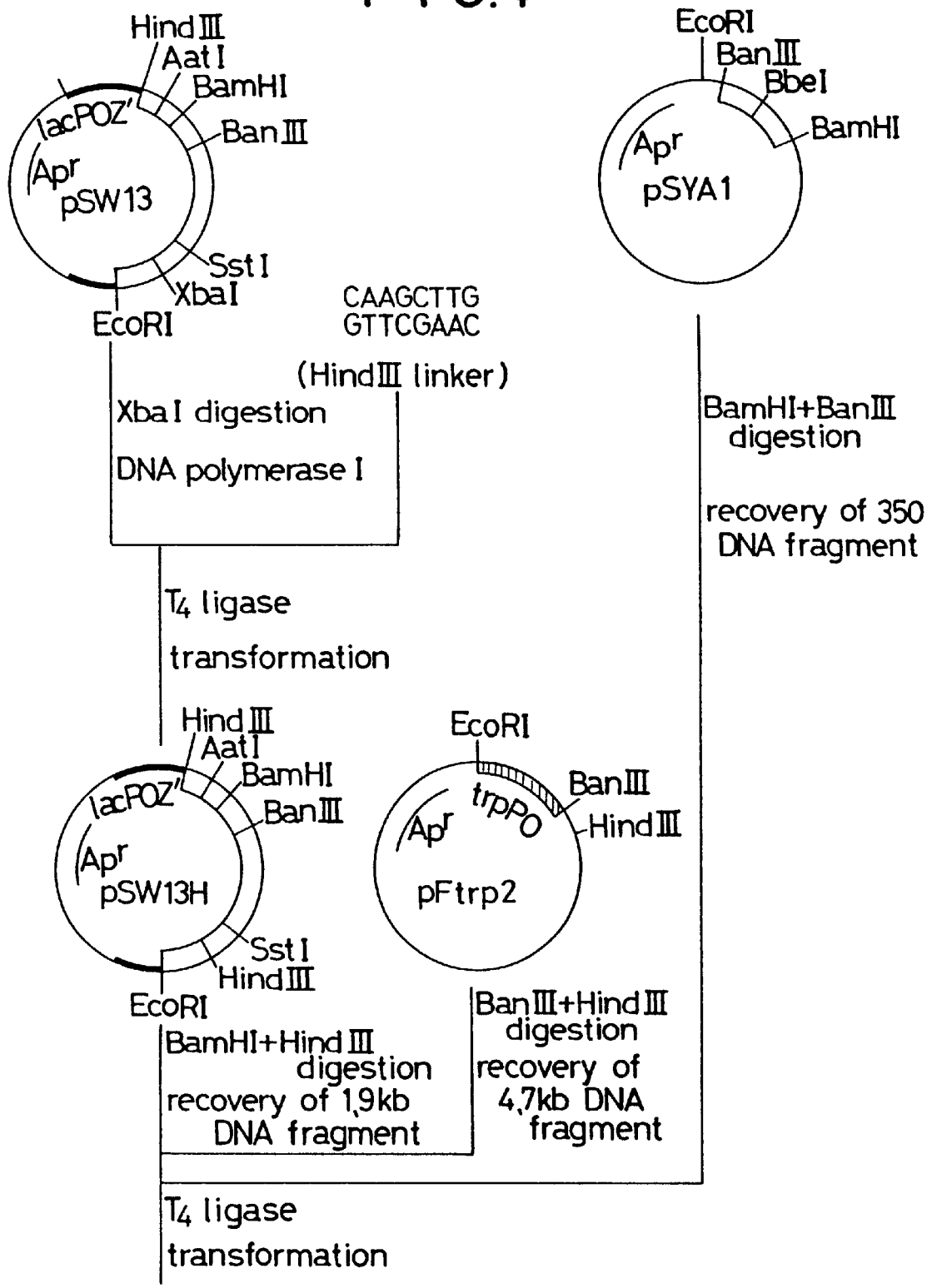

Next, the plasmid pFtrp2 constructed according to the procedure described in Reference Example 5 given later was digested with BanIII and HindIII. From the resulting fragment mixture, a fragment of 4.7 kb was recovered by agarose gel electrophoresis. To this 4.7 kb fragment were joined the previously prepared BamHI+BanIII fragment of 350 bp and the previously prepared BamHI+HindIII fragment of 1.9 kb by means of a ligase as shown in FIG. 4. Thus, a circular plasmid pSYA2 (FIG. 5) was constructed.

Moreover, pSYA2 was partially digested with BanIII and the resulting cohesive ends were treated with DNA polymerase to generate flush ends. Then, this fragment was cyclized by means of a ligase to create a plasmid pYtrp6 (FIG. 5) having a cleavage site for NruI.

Figure 3:
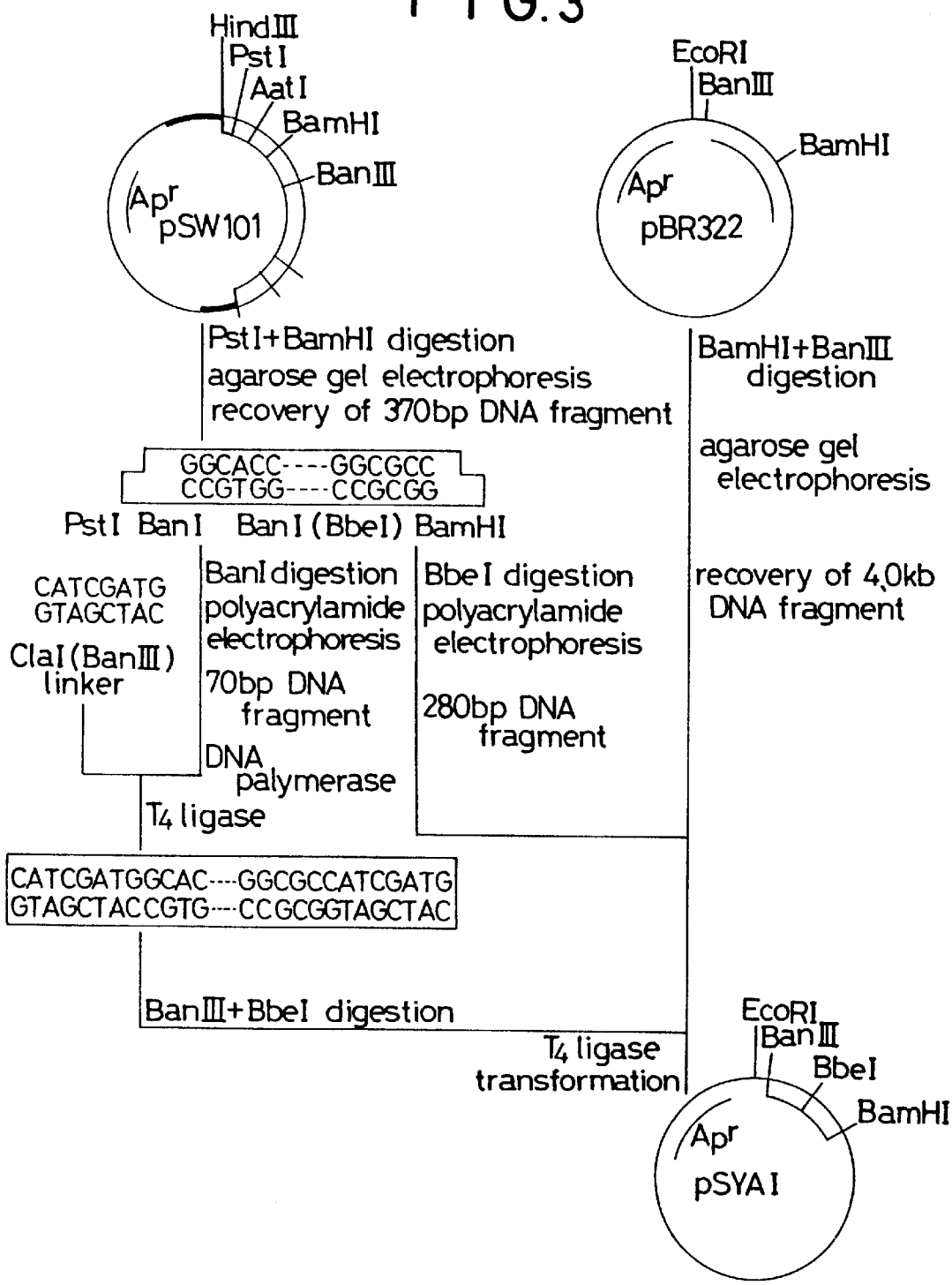
FIGS. 3, 4 and 5 are flow charts for the construction of pYtrp6 illustrating the respective parts. of the flow chart of FIG. 2 in more detail.
Figure 5:
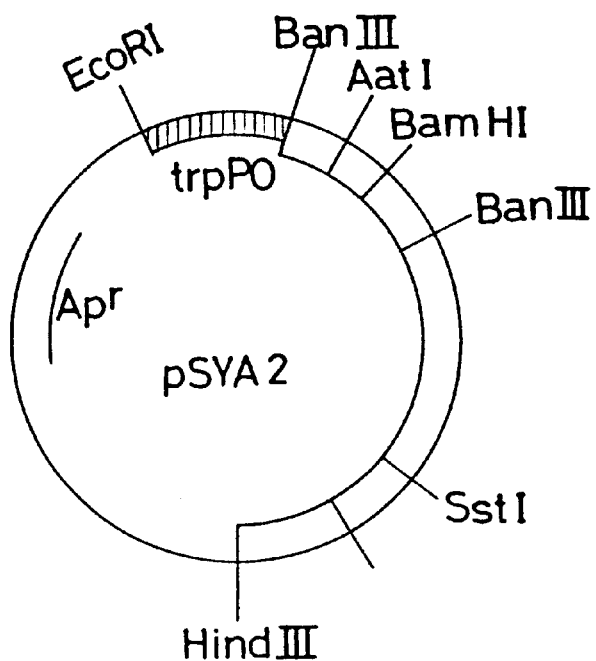
Figure 5:
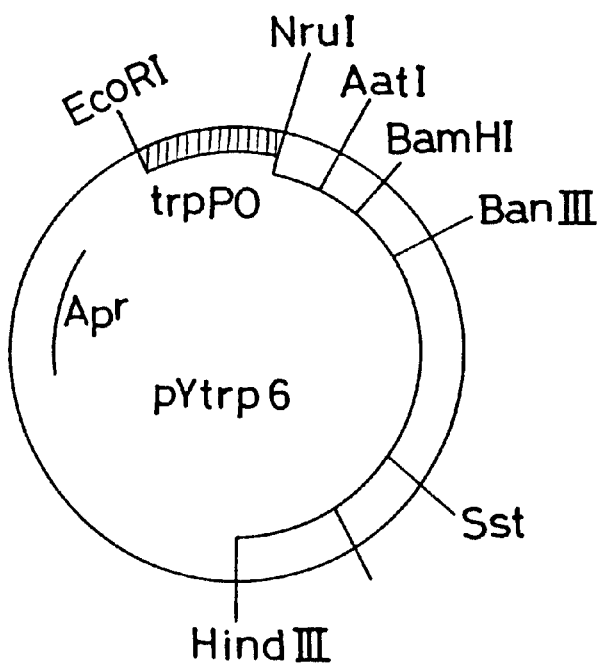

*E. coli* MC 1061 was transformed with pYtrp6 according to the well-known method. Cells were selected from the resulting ampicillin-resistant colonies and then tested for PAL activity. The construction of pYtrp6 is generally illustrated in the flow chart of FIG. 2 and its greater details are illustrated in FIGS. 3 to 5. The isolated transformant of *E. coli* exhibiting PAL-activity was named MT-10414 (FERM BP-1712).

10. Construction of pKY201 and Transformation

The plasmid pYtrp6 constructed in Section 9 above was digested with NruI and then treated with CIP. Then, HindIII linkers were joined thereto by means of a ligase, followed by digestion with HindIII. From the resulting fragment mixture, a DNA fragment of 2.3 kb was recovered by agarose gel electrophoresis.

On the other hand, the shuttle vector AHH5 of G. Ammerer (Reference 13), which replicates in both *E. coli* and bakers' yeast having ADHI (alcohol dehydrogenase I), was digested with HindIII and then treated with CIP. Using a ligase, the 2.3 kb DNA fragment previously prepared from pYtrp6 was inserted therein to construct plasmids.

Using these plasmids, *E. coli* MC 1061 was transformed according to the competent cell method. From cells exhibiting resistance to ampicillin, plasmids were extracted according to conventional procedure and a plasmid having the aforesaid DNA fragment inserted in the right direction was selected.

The plasmid which was shown by sequence analysis to have the aforesaid DNA fragment inserted in the right direction was named pKY201 (FIG. 6). Using this pKY201, an L-leucine-dependent strain (leu 2) of bakers' yeast (*Saccharomyces cerevisiae* MT-40391) was transformed according to the KU method (Reference 20). Then, the yeast was inoculated on YAL agar medium (composed of 0.67% Bacto Yeast Nitrogen Base, 0.5% glucose, 0.005% adenine sulfate, 0.05% L-lysine and 1.5% agar) that was a synthetic medium containing no L-leucine. After this medium was incubated at 25° C. for 3 days, cells were isolated from the formed colonies and tested for PAL activity. A cell strain exhibiting PAL activity was named MT-40390 (FERM BP-1711).

11. Production of PAL by a Transformant

LB medium containing ampicillin (0.1 mg/ml) was inoculated with a transformant (*E. coli* MT-10414). After the inoculated medium was shaken at 35° C. for 10 hours, a 10 mg/ml solution of indoleacrylic acid in ethanol was sterilely added thereto in such an amount that the medium would have an indoleacrylic acid concentration of 0.02 mg/ml.

After the addition of indoleacrylic acid, the medium was further shaken at 35° C. for 6 hours.

Thereafter, the resulting culture was centrifuged and the cells were recovered.

The cells were suspended in a 0.1 M Tris-HCl buffer solution (pH 8.5) and then disintegrated in a Dyno mill (Model KDL) containing glass beads of 0.25 mm diameter.

The resulting fluid was centrifuged and separated into a residue and a supernatant. Ammonium sulfate was added to the supernatant for purposes of salting-out. The precipitate so formed was dissolved in a 0.1 M Tris-HCl buffer solution (pH 8.5) and subjected to DEAE-cellulose column chromatography. A fraction exhibiting PAL activity was separated, purified by gel filtration, concentrated, and then used in the measurement of its molecular weight by polyacrylamide gel electrophoresis, immunoblotting using an antibody specific for PAL, and the measurement of its isoelectric point by isoelectrofticusing.

The protein of the fraction exhibiting PAL activity showed an antigen-antibody reaction with the antibody specific for PAL. Its molecular weight was about 77,000 when measured by SDS electrophoresis, and its isoelectric point (pI) was 5.5.

These values agreed with those for the PAL obtained from *R. toruloides*. This result confirmed the production of PAL.

12. Production of L-phenylalanine by use of a Transformant

M9 medium was prepared by dissolving 6 g of $Na_2HPO_4$, 3 g of $KH_2PO_4$, 0.5 g of NaCl and 1 g of $NH_4Cl$ in 1 liter of distilled water, adjusting the resulting solution to pH 7.5 with KOH, and autoclaving it at 120° C. for 10 minutes. Then, 2 ml of 1M $MgSO_4$, 10 ml of a 20% aqueous solution of glucose, and 0.1 ml. of 1M $CaCl_2$ were sterilized by filtration through a filter having a pore diameter of 0.22 $\mu$m (MILLEX-GS; a product of Millipore Ltd.), and added to 1 liter of the M9 medium. After the addition of ampicillin to a concentration of 0.1 mg/ml, the medium was inoculated with a transformant (*E. coli* MT-10414).

After the inoculated medium was incubated at 37° C. for 6 hours under aerated and stirred conditions, a 10 mg/ml solution of indoleacrylic acid in ethanol was sterilely added thereto in such an amount that the medium would have an indoleacrylic acid concentration of 0.02 mg/ml.

After the addition of indoleacrylic acid, the incubation was further continued at 37° C. for 4 hours under aerated and agitated conditions.

After that time, the resulting culture was centrifuged and the grown cells were collected.

A reaction medium was prepared by dissolving 4 g of cinnamic acid in 90 ml of aqueous ammonia, adjusting the resulting solution to pH 10.0 with sulfuric acid, and diluting it with distilled water to a volume of 195 ml. To this reaction medium were added 5 g of the grown cells. The resulting reaction mixture was kept at 30° C. for 20 hours, with gentle stirring, to react ammonia with cinnamic acid in the presence of the enzyme produced by the cells.

After that time, the reaction mixture was centrifuged and the cells were removed therefrom. The supernatant was concentrated under reduced pressure and the resulting concentrate was adjusted to pH 1.5–1.8 with sulfuric acid.

The precipitate of unreacted cinnamic acid formed under the $H_2SO_4$-acidified condition was removed by filtration, and the filtrate was passed through a column of Amberlite IR-120($H^+$). After completion of the passage, the resin column was washed with water and then back-washed with 0.25N aqueous ammonia. The resulting eluate was recovered and evaporated to dryness to obtain 2.8 g of crude L-phenylalanine. This product was identified as L-phenylalanine by means of an amino acid analyzer.

13. Production of L-phenylalanine by use of a Transformant

YAL synthetic medium (composed of 0.67% Bacto® Yeast Nitrogen Base, 1.0% glucose, 0.001% adenine sulfate, 0.005% L-lysine and 0.001% uracil) was sterilized by filtration through a sterilizing filter having pore diameter of 0.4 μm, and 200-ml portions thereof were poured into Sakaguchi flasks. This medium was inoculated with a transformant (*S. cerevisiae* MT-40390) and then shaken at 25° C. for 44 hours.

Four liters of the resulting culture was centrifuged to collect the cells. These cells were washed with cold water to obtain washed cells.

A reaction medium was prepared by dissolving 4 g of cinnamic acid in 90 ml of aqueous ammonia, adjusting the resulting solution to pH 9.5 with hydrochloric acid, and diluting it with distilled water to a volume of 190 ml. To this reaction medium were added 10 g of the washed cells. The resulting reaction mixture was kept at 30° C. for 36 hours, with gentle stirring, to effect the reaction.

After that time, the reaction mixture was concentrated under reduced pressure and the resulting concentrate was adjusted to pH 2 or below with hydrochloric acid. This solution was allowed to stand at 10° C. for 9 hours and the resulting precipitate of unreacted cinnamic acid and insolubilized cells was removed by filtration. Then, the filtrate was mixed with an equal volume of tributyl phosphate to extract cinnamic acid therefrom.

After extraction, the aqueous phase was concentrated to dryness under reduced pressure to obtain 4 g of solid material. This solid material was dissolved in dilute hydrochloric acid. After the addition of 1 g of activated carbon, the resulting mixture was heated at 90° C. for 10 minutes and then filtered to remove the activated carbon. Thus, there was obtained a clear solution.

This solution was adjusted to pH 6.0 with aqueous ammonia and then cooled to precipitate crystals of L-phenylalanine. After these crystals were separated by filtration, the filtrate was cooled again and the precipitated crystals were recovered and combined with the previously obtained crystals of L-phenylalanine, followed by drying under reduced pressure. Eventually, there was obtained 2.0 g of L-phenylalanine in the form of crystals.

14. Production of L-phenylalanine by use of L-phenylalanine Ammonia-lyase

A microorganism was grown in the same manner as described in Section 11 above. From 30 g of the collected and washed cells, L-phenylalanine ammonia-lyase was extracted and purified according to the same procedure as described in Section 11 above. The purified L-phenylalanine ammonia-lyase was dissolved in 20 ml of a $NH_4OH$—$(NH_4)_2SO_4$ buffer solution (pH 10.0) containing 8M $NH$ The resulting solution was placed in a dialysis tube (a product of Union Carbide Corp.), which was sealed at both ends. This tube was immersed in a reaction mixture prepared by adding 4 g of cinnamic acid to 200 ml of a $NH_4OH$—$(NH_4)_2SO_4$ buffer solution (pH 10.0) containing 8M $NH_3$. The reaction was carried out at 30° C. for 40 hours with gentle stirring of the outer liquid. After that time, the procedure of Section 13 was repeated to obtain 2.0 g of L-phenylalanine.

REFERENCE EXAMPLE 1

[Cloning of the Chromosomal DNA Coding for the PAL of *Rhodosporidium toruloides*]

The chromosomal DNA of *Rhodosporidium toruloides* was prepared according to the procedure of Gilbert et al. (Reference 21). More specifically, chromosomal DNA was extracted from the microorganism and then cleaved with the restriction endonucleases PstI and BclI. The resulting DNA fragments were subjected to agarose gel electrophoresis, and a DNA fragment having a size of 5.6 kb was recovered from the gel by electrodialysis.

Using a ligase, this DNA fragment was joined to pBR322 which had been cleaved with the restriction endonuclease PstI. Thus, a hybrid plasmid comprising pBR322 having the chromosomal DNA for PAL inserted therein was assembled.

Using this hybrid plasmid, *E. coli* MC 1061 was transformed to obtain transformed cells of *E. coli*. From the transformed. cells, plasmid DNA was extracted and purified according to a rapid plasmid extraction method (Reference 22). Then, by treating the plasmid DNA with various restriction endonucleases, the structure of the plasmid was examined.

REFERENCE EXAMPLE 2

[Synthesis of $^{32}$P-labeled Single-stranded DNA for PAL]

In synthesizing single-stranded cDNA from the mRNA for PAL according to the procedure described in Section 2 of the Example, α-$^{32}$P-dCTP was used in place of the dCTP present in the reaction mixture. Thus, there was obtained $^{32}$P-labeled single-stranded cDNA.

This labeled single-stranded cDNA was treated with RNaseH to digest the mRNA. Then, DNA was recovered by treatment with phenol and precipitation with cold ethanol. The single-stranded cDNA thus obtained was used as a probe in Reference Example 3.

REFERENCE EXAMPLE 3

[Detection of *E. coli* Transformants Containing a Hybrid Plasmid Composed of the Chromosomal DNA for PAL and pBR322]

The *E. coli* transformants obtained according to the procedure described in Reference Example 1 were subjected to a colony hybridization process using the $^{32}$P-labeled single-stranded cDNA prepared in Reference Example 2 as the probe (Reference 23).

Positive colonies were selected from among the *E. coli* transformants, and plasmid was extracted and purified from these colonies according to conventional procedure. After the plasmid was treated with various restriction endonucleases, the resulting DNA fragment mixture was subjected to agarose gel electrophoresis. Thus, a restriction endonuclease cleavage map of the plasmid was constructed.

Moreover, the following procedure was employed to confirm that the gene coding for PAL is inserted in the plasmid. First, the plasmid was cleaved with the restriction endonuclease BamHI. The resulting DNA fragment mixture was subjected to agarose gel electrophoresis, and a DNA fragment having a size of 3 kb was recovered. From this DNA fragment, a P-labeled DNA probe was prepared according to the nick translation method using spleen DNase I, *E. coli* DNA polymerase I and a- P-DCTP.

On the other hand, the purified mRNA prepared in Section 1 of the Example and containing the mRNA for PAL was denatured by treatment with glyoxal, and then subjected to agarose gel electrophoresis. After completion of the electrophoresis, the mRNA was transferred from the gel to nylon paper and then subjected to a northern hybridization process using the aforesaid $^{32}$P-labeled DNA probe (Reference 24). Thus, it was confirmed that the aforesaid hybrid plasmid contained the PAL gene.

REFERENCE EXAMPLE 4
[Confirmation of the Size of the DNA Coding for the PAL gene]

The hybrid plasmid, which contained the chromosomal DNA for PAL as confirmed by the procedure described in Reference Example 3, was extracted and purified from *E. coli* transformants, and then treated with various restriction endonucleases. After the resulting DNA fragment mixture was subjected to agarose gel electrophoresis, the fractionated DNA fragments were transferred to a nitrocellulose filter and then subjected to a DNA-DNA hybridization process using a probe comprising the $^{32}$ P-labeled single-stranded cDNA for PAL prepared according to the procedure of Reference Example 2.

REFERENCE EXAMPLE 5
[Assembly of the Tryptophan (trp) Promoter Region]

The plasmid pVV1 containing a part of the trp operon of *E. coli* was digested with the restriction endonuclease HinfI.

The DNA fragments of the digested plasmid were separated by agarose gel electrophoresis, and a DNA fragment having a size of 0.9 kb was recovered from the gel according to the procedure described in Section 1 of the Example.

The cohesive ends of the 0.9 kb DNA fragment generated by digestion with HinfI were converted to flush ends according to the procedure described in Section 8 of the Example. Then, an EcoRI linker (GGAATTCC) was joined to the 5'-flush end by means of a ligase.

The DNA fragment having an EcoRI linker joined thereto was treated with the restriction endonuclease EcoRI to create a DNA fragment having an EcoRI-cleaved cohesive end (Reference 25).

Using a ligase, the DNA fragment having an EcoRI cohesive end was joined to a DNA fragment which had been obtained by treating the EcoRI digest of pBR322 with CIP according to the procedure described in Section 8 of the Example. The resulting product was digested with the restriction endonucleases EcoRI and BglII. The resulting digest was subjected to agarose gel electrophoresis, and a DNA fragment having a size of 0.4 kb was separated and recovered.

This DNA fragment, which had three cleavage sites for the restriction endonuclease TaqI, was partially digested with TaqI. Thus, a DNA fragment having a size of 345 bp was recovered.

This 345 bp DNA fragment was joined to a 3.4 kb DNA fragment obtained by digesting pBR322 with EcoRI and ClaI. Thus, there was obtained a plasmid pFtrp2 containing the trp promoter.

REFERENCE EXAMPLE 6
[Determination of PAL Activity]

A microorganism containing a plasmid capable of producing PAL was grown. If necessary, it was subjected to an induction treatment for enhancing the function of the promoter of the plasmid. Thereafter, the grown cells were collected.

In order to destroy the cell wall and solubilize the intracellular enzymes, the cells were subjected to a mechanical treatment such as sonication or glass bead disintegration, or a chemical procedure such as treatment with a bacteriolytic enzyme or a surface active agent. Thus, there was obtained a cell extract.

Thereafter, the cell extract was centrifuged and the resulting supernatant was used as a sample.

Since PAL activity is represented by the enzymatic reaction forming cinnamic acid from L-phenylalanine, the aforesaid supernatant was diluted with a 25 mM Tris-HCl buffer solution (pH 8.8), and 1.0 ml of the diluted supernatant was added to 5.0 ml of an enzymatic reaction medium [i.e., a 25 mM Tris-HCl buffer solution (pH 8.8) containing 10 mM L-phenylalanine. The resulting reaction mixture was incubated at 30° C. for 20 minutes and then examined for PAL activity.

More specifically, the reaction was stopped by the addition of 1 ml of 1N HCl and the formed cinnamic acid was detected by liquid chromatography.

The liquid chromatography was carried out by using Column YMC Pack A-312 (a product of Yamamura Chemical Laboratory Co.) as the separating column. For purposes of detection, an ultraviolet spectrophotometer was used at a detection wavelength of 260 nm.

REFERENCE EXAMPLE 7
[Formation of *S. serevisiae* MT-40391]

*S. serevisiae* MT-40391 was obtained by nutating *S. serevisiae* ATCC 44771 and selecting the lysine-dependent strain according to the method of Sherman, F., et al (Reference 28).

```
Amino acid sequence of PAL 1                                              10
Met Ala Pro Ser Leu Asp Ser Ile Ser His
11                                             20
Ser Phe Ala Asn Gly Val Ala Ser Ala Lys
21                                             30
Gln Ala Val Asn Gly Ala Ser Thr Asn Leu
31                                             40
Ala Val Ala Gly Ser His Leu Pro Thr Thr
41                                             50
Gln Val Thr Gln Val Asp Ile Val Glu Lys
51                                             60
Met Leu Ala Ala Pro Thr Asp Ser Thr Leu
61                                             70
Glu Leu Asp Gly Tyr Ser Leu Asn Leu Gly
71                                             80
Asp Val Val Ser Ala Ala Arg Lys Gly Arg
81                                             90
Pro Val Arg Val Lys Asp Ser Asp Glu Ile
91                                            100
Arg Ser Lys Ile Asp Lys Ser Val Glu Phe
101                                           110
Leu Arg Ser Gln Leu Ser Met Ser Val Tyr
111                                           120
Gly Val Thr Thr Gly Phe Gly Gly Ser Ala
121                                           130
Asp Thr Arg Thr Glu Asp Ala Ile Ser Leu
131                                           140
Gln Lys Ala Leu Leu Glu His Gln Leu Cys
141                                           150
Gly Val Leu Pro Ser Ser Phe Asp Ser Phe
151                                           160
Arg Leu Gly Arg Gly Leu Glu Asn Ser Leu
161                                           170
Pro Leu Glu Val Val Arg Gly Ala Met Thr
```

```
171                            180
Ile Arg Val Asn Ser Leu Thr Arg Gly His
181                            190
Ser Ala Val Arg Leu Val Val Leu Glu Ala
191                            200
Leu Thr Asn Phe Leu Asn His Gly Ile Thr
201                            210
Pro Ile Val Pro Leu Arg Gly Thr Ile Ser
211                            220
Ala Ser Gly Asp Leu Ser Pro Leu Ser Tyr
221                            230
Ile Ala Ala Ile Ser Gly His Pro Asp
231                            240
Ser Lys Val His Val His Glu Gly Lys
251                            260
Ala Leu Phe Asn Leu Glu Pro Val Val Leu
261                            270
Gly Pro Lys Glu Gly Leu Gly Leu Val Asn
271                            280
Gly Thr Ala Val Ser Ala Ser Met Ala Thr
281                            290
Leu Ala Leu His Asp Ala His Met Leu Ser
291                            300
Leu Leu Ser Gln Ser Leu Thr Ala Met Thr
301                            310
Val Glu Ala Met Val Gly His Ala Gly Ser
311                            320
Phe His Pro Phe Leu His Asp Val Thr Arg
321                            330
Pro His Pro Thr Gln Ile Glu Val Ala Gly
331                            340
Asn Ile Arg Lys Leu Leu Glu Gly Ser Arg
341                            350
Phe Ala Val His His Glu Glu Glu Val Lys
351                            360
Val Lys Asp Asp Glu Gly Ile Leu Arg Gln
361                            370
Asp Arg Tyr Pro Leu Arg Thr Ser Pro Gln
371                            380
Trp Leu Gly Pro Leu Val Ser Asp Leu Ile
381                            390
His Ala His Ala Val Leu Thr Ile Glu Ala
391                            400
Gly Gln Ser Thr Thr Asp Asn Pro Leu Ile
401                            410
Asp Val Glu Asn Lys Thr Ser His His Gly
411                            420
Gly Asn Phe Gln Ala Ala Ala Val Ala Asn
421                            430
Thr Met Glu Lys Thr Arg Leu Gly Leu Ala
431                            440
Gln Ile Gly Lys Leu Asn Phe Thr Gln Leu
441                            450
Thr Glu Met Leu Asn Ala Gly Met Asn Arg
451                            460
Gly Leu Pro Ser Cys Leu Ala Ala Glu Asp
461                            470
Pro Ser Leu Ser Tyr His Cys Lys Gly Leu
471                            480
Asp Ile Ala Ala Ala Tyr Thr Ser Glu
481                            490
Leu Gly His Leu Ala Asn Pro Val Thr Thr
491                            500
His Val Gln Pro Ala Glu Met Ala Asn Gln
501                            510
Ala Val Asn Ser Leu Ala Leu Ile Ser Ala
511                            520
Arg Arg Thr Thr Glu Ser Asn Asp Val Leu
521                            530
Ser Leu Leu Leu Ala Thr His Leu Tyr Cys
531                            540
Val Leu Gln Ala Ile Asp Leu Arg Ala Ile
541                            550
Glu Phe Glu Phe Lys Lys Gln Phe Gly Pro
551                            560
Ala Ile Val Ser Leu Ile Asp Gln His Phe
561                            570
Gly Ser Ala Met Thr Gly Ser Asn Leu Arg
571                            580
Asp Glu Leu Val Glu Lys Val Asn Lys Thr
581                            590
Leu Ala Lys Arg Leu Glu Gln Thr Asn Ser
591                            600
Tyr Asp Leu Val Pro Arg Trp His Asp Ala
601                            610
Phe Ser Phe Ala Ala Gly Thr Val Val Glu
611                            620
Val Leu Ser Ser Thr Ser Leu Ser Leu Ala
621                            630
Ala Val Asn Ala Trp Lys Val Ala Ala Ala
631                            640
Glu Ser Ala Ile Ser Leu Thr Arg Gln Val
641                            650
Arg Glu Thr Phe Trp Ser Ala Ala Ser Thr
651                            660
Ser Ser Pro Ala Leu Ser Tyr Leu Ser Pro
661                            670
Arg Thr Gln Ile Leu Tyr Ala Phe Val Arg
671                            680
Glu Glu Leu Gly Val Lys Ala Arg Arg Gly
681                            690
Asp Val Phe Leu Gly Lys Gln Glu Val Thr
691                            700
Ile Gly Ser Asn Val Ser Lys Ile Tyr Glu
701                            710
Ala Ile Lys Ser Gly Arg Ile Asn Asn Val
711        716
Leu Leu Lys Met Leu Ala

DNA sequence of the structural gene for PAL 1                              10
ATG GCA CCC TCG CTC GAC TCG ATC TCG CAC
Met Ala Pro Ser Leu Asp Ser Ile Ser His
11                             20
TCG TTC GCA AAC GGC GTC GCA TCC GCA AAG
Ser Phe Ala Asn Gly Val Ala Ser Ala Lys
21                             30
CAG GCT GTC AAT GGC GCC TCG ACC AAC CTC
Gln Ala Val Asn Gly Ala Ser Thr Asn Leu
31                             40
GCA GTC GCA GGC TCG CAC CTG CCC ACA ACC
Ala Val Ala Gly Ser His Leu Pro Thr Thr
41                             50
CAG GTC ACG CAG GTC GAC ATC GTC GAG AAG
Gln Val Thr Gln Val Asp Ile Val Glu Lys
51                             60
ATG CTC GCC GCG CCG ACC GAC TCG ACG CTC
Met Leu Ala Ala Pro Thr Asp Ser Thr Leu
61                             70
GAA CTC GAC GGC TAC TCG CTC AAC CTC GGA
Glu Leu Asp Gly Tyr Ser Leu Asn Leu Gly
71                             80
GAC GTC GTC TCG GCC GCG AGG AAG GGC AGG
Asp Val Val Ser Ala Ala Arg Lys Gly Arg
81                             90
CCT GTC CGC GTC AAG GAC AGC GAC GAG ATC
Pro Val Arg Val Lys Asp Ser Asp Glu Ile
91                             100
CGC TCA AAG ATT GAC AAA TCG GTC GAG TTC
Arg Ser Lys Ile Asp Lys Ser Val Glu Phe
101                            110
TTG CGC TCG CAA CTC TCC ATG AGC GTC TAC
Leu Arg Ser Gln Leu Ser Met Ser Val Tyr
111                            120
GGC GTC ACG ACT GGA TTT GGC GGA TCC GCA
Gly Val Thr Thr Gly Phe Gly Gly Ser Ala
121                            130
GAC ACC CGC ACC GAG GAC GCC ATC TCG CTC
Asp Thr Arg Thr Glu Asp Ala Ile Ser Leu
131                            140
CAG AAG GCT CTC CTC GAG CAC CAG CTC TGC
Gln Lys Ala Leu Leu Glu His Gln Leu Cys
141                            150
GGT GTT CTC CCT TCG TCG TTC GAC TCG TTC
Gly Val Leu Pro Ser Ser Phe Asp Ser Phe
151                            160
CGC CTC GGC CGC GGT CTC GAG AAC TCG CTT
Arg Leu Gly Arg Gly Leu Glu Asn Ser Leu
```

```
161                                    170
CCC CTC GAG GTT GTT CGC GGC GCC ATG ACA
Pro Leu Glu Val Val Arg Gly Ala Met Thr
171                                    180
ATC CGC GTC AAC AGC TTG ACC CGC GGC CAC
Ile Arg Val Asn Ser Leu Thr Arg Gly His
181                                    190
TCG GCT GTC CGC CTC GTC GTC CTC GAG GCG
Ser Ala Val Arg Leu Val Val Leu Glu Ala
191                                    200
CTC ACC AAC TTC CTC AAC CAC GGC ATC ACC
Leu Thr Asn Phe Leu Asn His Gly Ile Thr
201                                    210
CCC ATC GTC CCC CTC CGC GGC ACC ATC TCT
Pro Ile Val Pro Leu Arg Gly Thr Ile Ser
211                                    220
GCG TCG GGC GAC CTC TCT CCT CTC TCC TAC
Ala Ser Gly Asp Leu Ser Pro Leu Ser Tyr
221                                    230
ATT GCA GCG GCC ATC AGC GGT CAC CCG GAC
Ile Ala Ala Ala Ile Ser Gly His Pro Asp
231                                    240
AGC AAG GTG CAC GTC GTC CAC GAG GGC AAG
Ser Lys Val His Val Val His Glu Gly Lys
241                                    250
GAG AAG ATC CTG TAC GCC CGC GAG GCG ATG
Glu Lys Ile Leu Tyr Ala Arg Glu Ala Met
251                                    260
GCG CTC TTC AAC CTC GAG CCC GTC GTC CTC
Ala Leu Phe Asn Leu Glu Pro Val Val Leu
261                                    270
GGC CCG AAG GAA GGT CTC GGT CTC GTC AAC
Gly Pro Lys Glu Gly Leu Gly Leu Val Asn
271                                    280
GGC ACC GCC GTC TCA GCA TCG ATG GCC ACC
Gly Thr Ala Val Ser Ala Ser Met Ala Thr
281                                    290
CTC GCT CTG CAC GAC GCA CAC ATG CTC TCG
Leu Ala Leu His Asp Ala His Met Leu Ser
291                                    300
CTC CTC TCG CAG TCG CTC ACG GCC ATG ACG
Leu Leu Ser Gln Ser Leu Thr Ala Met Thr
301                                    310
GTC GAA GCG ATG GTC GGC CAC GCC GGC TCG
Val Glu Ala Met Val Gly His Ala Gly Ser
311                                    320
TTC CAC CCC TTC CTT CAC GAC GTC ACG CGC
Phe His Pro Phe Leu His Asp Val Thr Arg
321                                    330
CCT CAC CCG ACG CAG ATC GAA GTC GCG GGA
Pro His Pro Thr Gln Ile Glu Val Ala Gly
331                                    320
AAC ATC CGC AAG CTC CTC GAG GGA AGC CGC
Asn Ile Arg Lys Leu Leu Glu Gly Ser Arg
341                                    350
TTT GCT GTC CAC CAT GAG GAG GAG GTC AAG
Phe Ala Val His His Glu Glu Glu Val Lys
351                                    360
GTC AAG GAC GAC GAG GGC ATT CTC CGC CAG
Val Lys Asp Asp Glu Gly Ile Leu Arg Gln
361                                    370
GAC CGC TAC CCC TTG CGC ACG TCT CCT CAG
Asp Arg Tyr Pro Leu Arg Thr Ser Pro Gln
371                                    380
TGG CTC GGC CCG CTC GTC AGC GAC CTC ATT
Trp Leu Gly Pro Leu Val Ser Asp Leu Ile
381                                    390
CAC GCC CAC GCC GTC CTC ACC ATC GAG GCC
His Ala His Ala Val Leu Thr Ile Glu Ala
391                                    400
GGC CAG TCG ACG ACC GAC AAC CCT CTC ATC
Gly Gln Ser Thr Thr Asp Asn Pro Leu Ile
401                                    410
GAC GTC GAG AAC AAG ACT TCG CAC CAC GGC
Asp Val Glu Asn Lys Thr Ser His His Gly
411                                    420
GGC AAT TTC CAG GCT GCC GCT GTG GCC AAC
Gly Asn Phe Gln Ala Ala Ala Val Ala Asn
421                                    430
ACC ATG GAG AAG ACT CqC CTC GGG CTC GCC
Thr Met Glu Lys Thr Arg Leu Gly Leu Ala
431                                    440
CAG ATC GGC AAG CTC AAC TTC ACG CAG CTC
Gln Ile Gly Lys Leu Asn Phe Thr Gln Leu
441                                    450
ACC GAG ATG CTC AAC GCC GGC ATG AAC CGC
Thr Glu Met Leu Asn Ala Gly Met Asn Arg
451                                    460
GGC CTC CCC TCC TGC CTC GCG GCC GAA GAC
Gly Leu Pro Ser Cys Leu Ala Ala Glu Asp
461                                    470
CCC TCG CTC TCC TAC CAC TGC AAG GGC CTC
Pro Ser Leu Ser Tyr His Cys Lys Gly Leu
471                                    480
GAC ATC GCC GCT GCG GCG TAC ACC TCG GAG
Asp Ile Ala Ala Ala Ala Tyr Thr Ser Glu
481                                    490
TTG GGA CAC CTC GCC AAC CCT GTG ACG ACG
Leu Gly His Leu Ala Asn Pro Val Thr Thr
491                                    500
CAT GTC CAG CCG GCT GAG ATG GCG AAC CAG
His Val Gln Pro Ala Glu Met Ala Asn Gln
501                                    510
GCG GTC AAC TCG CTT GCG CTC ATC TCG GCT
Ala Val Asn Ser Leu Ala Leu Ile Ser Ala
511                                    520
CGT CGC ACG ACC GAG TCC AAC GAC GTC CTT
Arg Arg Thr Thr Glu Ser Asn Asp Val Leu
521                                    530
TCT CTC CTC CTC GCC ACC CAC CTC TAC TGC
Ser Leu Leu Leu Ala Thr His Leu Tyr Cys
531                                    540
GTT CTC CAA GCC ATC GAC TTG CGC GCG ATC
Val Leu Gln Ala Ile Asp Leu Arg Ala Ile
541                                    550
GAG TTC GAG TTC AAG AAG CAG TTC GGC CCA
Glu Phe Glu Phe Lys Lys Gln Phe Gly Pro
551                                    560
GCC ATC GTC TCG CTC ATC GAC CAG CAC TTT
Ala Ile Val Ser Leu Ile Asp Gln His Phe
561                                    570
GGC TCC GCC ATG ACC GGC TCG AAC CTG CGC
Gly Ser Ala Met Thr Gly Ser Asn Leu Arg
571                                    580
GAC GAG CTC GTC GAG AAG GTG AAC AAG ACG
Asp Glu Leu Val Glu Lys Val Asn Lys Thr
581                                    590
CTC GCC AAG CGC CTC GAG CAG ACC AAC TCG
Leu Ala Lys Arg Leu Glu Gln Thr Asn Ser
591                                    600
TAC GAC CTC GTC CCG CGC TGG CAC GAC GCC
Tyr Asp Leu Val Pro Arg Trp His Asp Ala
601                                    610
TTC TCC TTC GCC GCC GGC ACC GTC GTC GAG
Phe Ser Phe Ala Ala Gly Thr Val Val Glu
611                                    620
GTC CTC TCG TCG ACG TCG CTC TCG CTC GCC
Val Leu Ser Ser Thr Ser Leu Ser Leu Ala
621                                    630
GCC GTC AAC GCC TGG AAG GTC GCC GCC GCC
Ala Val Asn Ala Trp Lys Val Ala Ala Ala
631                                    640
GAG TCG GCC ATC TCG CTC ACC CGC CAA GTC
Glu Ser Ala Ile Ser Leu Thr Arg Gln Val
641                                    650
CGC GAG ACC TTC TGG TCC GCC GCG TCG ACC
Arg Glu Thr Phe Trp Ser Ala Ala Ser Thr
651                                    660
TCG TCG CCC GCG CTC TCG TAC CTC TCG CCG
Ser Ser Pro Ala Leu Ser Tyr Leu Ser Pro
661                                    670
CGC ACT CAG ATC CTC TAC GCC TTC GTC CGC
Arg Thr Gln Ile Leu Tyr Ala Phe Val Arg
671                                    680
GAG GAG CTT GGC GTC AAG GCC CGC CGC GGA
Glu Glu Leu Gly Val Lys Ala Arg Arg Gly
```

```
                          -continued
681                                                  690
GAC GTC TTC CTC GGC AAG CAA GAG GTG ACG
Asp Val Phe Leu Gly Lys Gln Glu Val Thr
691                                                  700
ATC GGC TCG AAC GTC TCC AAG ATC TAC GAG
Ile Gly Ser Asn Val Ser Lys Ile Tyr Glu
701                                                  710
GCC ATC AAG TCG GGC AGG ATC AAC AAC GTC
Ala Ile Lys Ser Gly Arg Ile Asn Asn Val
711                     716 717
CTC CTC AAG ATG CTC GCT TAG ACA CT CTTCC
Leu Leu Lys Met Leu Ala STOP
CACTCTCGCA TCCCTTCCAT ACCCTATCCC GCCTGCACTC
TTAGGACTCG CTTCTTGTCG GACTCGGATC TCGCATCGCT
TCTTTCGTTC TTGGCTGCCT CTCTAGACCG TGTCGGTATT
ACCTCGAGAT TGTGAATACA AGCAGTACCC ATCCAAAAAA
AAAAAA---AAA
```

List of References

1. Hallewell, R. H. et al., Gene, 9, 27–47, (1980)
2. Nichols, B. P. et al., Methods in Enzymology, 101, 155–164, (1983)
3. Russell, D. R. et al., Gene, 17, 9–18, (1982)
4. Japanese Patent Laid-Open No. 91987/'85
5. Fuller, F., Gene, 19, 43, (1982)
6. de Boer, H. A. et al., Proc. Natl. Acad. Sci. USA, 80, 21, (1983)
7. H. Schimatake et al., "Nature", 292, 128-(1981).
8. J. A. Lautenberger et al., "Gene", 23, 75-(1983).
9. Christie, G. E. et al., Proc. Natl. Acad. Sci. USA, 78, 4180, (1980)
10. Struhl. K. et al., Proc. Natl. Acad. Sci. USA, 76, 1035–1039, (1979)
11. Dobson, M. J. et al., Nucleic Acids Research, 10, 2625–2637, (1982)
12. Holland, J. P et al., J. Biol. Chem., 255, 2596, (1980)
13. Ammerer, G., Methods in Enzymolozy, 101, 192–201, (1983)
14. Wickerham, L. J., Taxonomy of yeasts, United States Department of Agriculture, Technical Bulletin, No. 1029, 1, (1951)
15. Maniatis. T. et al., "Molecular Cloning" (1982)
16. Pelham. H. R. et al., European J. Biochem., 67, 247–256, (1976)
17. Laemmli, Nature, 227, 680–685, (1970)
18. Gubber, U. et al., Gene, 25, 263–269, (1983)
19. Maat, J. et al., Nucleic Acids Research, 5, 4537–4545, (1978)
20. H. Ito et al., J. of Bacteriol.,153, 163(1983)
21. Gilbert, H. J. et al., J. of Bacteriology, 161, 314–320, (1985)
22. Birnboim, H. C. et al., Nucleic Acids Research, 1, 1513–1523, (1979)
23. Grunstein, M. et al., Proc. Natl. Acad. Sci. USA., 72, 3961, (1971)
24. Thomas, P. S., Methods in Enzymology, 100, 255, (1983)
25. Nichols, B. P. et al., Methods in Enzymology, 101, 155, (1983)
26. Casadaban, M. J., et al., Methods in Enzymology, 100, 293–308, (1983)
27. Messing, J. and Vieira J., Gene, 19, 259–268, (1982)
28. Sherman, F., et al., Methods in Yeast Genetics (Laboratory Manual), Cold Spring Harbor Laboratory, New York (1982)

Among the microorganims strains, the strains having an ATCC number are deposited in the American Type Culture Collection, 12301 Parklawn Drive, Rockville, Md. 20852-1776, U.S.A.; and those having an FERM number are deposited in the Fermentation Research Institute of the Agency of Industrial Science and Technology, 1–3, Higashi 1-chome, Yatabe-machi, Tsukuba-gun, Ibaraki-ken, 305, JAPAN.

What is claimed is:

1. Recombinant L-phenylalanine ammonia-lyase produced by a transformant having a recombinant DNA plasmid comprising an expression vector having a construction permitting a polypeptide to be expressed in *Escherichia coli*, the expression vector having incorporated therein a DNA strand whose sequence codes for a polypeptide derived from *Rhodosporidium toruloides* having the following amino acid sequence:

```
1                                                     10
Met Ala Pro Ser Leu Asp Ser Ile Ser His
11                                                    20
Ser Phe Ala Asn Gly Val Ala Ser Ala Lys
21                                                    30
Gln Ala Val Asn Gly Ala Ser Thr Asn Leu
31                                                    40
Ala Val Ala Gly Ser His Leu Pro Thr Thr
41                                                    50
Gln Val Thr Gln Val Asp Ile Val Glu Lys
51                                                    60
Met Leu Ala Ala Pro Thr Asp Ser Thr Leu
61                                                    70
Glu Leu Asp Gly Tyr Ser Leu Asn Leu Gly
71                                                    80
Asp Val Val Ser Ala Ala Arg Lys Gly Arg
81                                                    90
Pro Val Arg Val Lys Asp Ser Asp Glu Ile
91                                                    100
Arg Ser Lys Ile Asp Lys Ser Val Glu Phe
101                                                   110
Leu Arg Ser Gln Leu Ser Met Ser Val Tyr
111                                                   120
Gly Val Thr Thr Gly Phe Gly Gly Ser Ala
121                                                   130
Asp Thr Arg Thr Glu Asp Ala Ile Ser leu
131                                                   140
Gln Lys Ala Leu Leu Glu His Gln Leu Cys
141                                                   150
Gly Val Leu Pro Ser Ser Phe Asp Ser Phe
151                                                   160
Arg Leu Gly Arg Gly Leu Glu Asn Ser Leu
161                                                   170
Pro Leu Glu Val Val Arg Gly Ala Met Thr
171                                                   180
Ile Arg Val Asn Ser Leu Thr Arg Gly His
181                                                   190
Ser Ala Val Arg leu Val Val Leu Glu Ala
191                                                   200
Leu Thr Asn Phe Leu Asn His Gly Ile Thr
201                                                   210
Pro Ile Val Pro Leu Arg Gly Thr Ile Ser
211                                                   220
Ala Ser Gly Asp Leu Ser Pro Leu Ser Tyr
221                                                   230
Ile Ala Ala Ala Ile Ser Gly His Pro Asp
231                                                   240
Ser Lys Val His Val Val His Glu Gly Lys
241                                                   250
Glu Lys Ile Leu Tyr Ala Arg Glu Ala Met
251                                                   260
Ala Leu Phe Asn Leu Glu Pro Val Val Leu
261                                                   270
Gly Pro Lys Glu Gly Leu Gly Leu Val Asn
271                                                   280
Gly Thr Ala Val Ser Ala Ser Met Ala Thr
281                                                   290
Leu Ala Leu His Asp Ala His Met Ala Thr
```

```
                    -continued
291                                          300
Leu Leu Ser Gln Ser Leu Thr Ala Met Thr
301                                          310
Vla Glu Ala Met Val Gly his Ala Gly Ser
311                                          320
Phe His Pro Phe Leu His Asp Val Thr Arg
321                                          330
Pro His Pro Thr Gln Ile Glu Val Ala Gly
331                                          340
Asn Ile Arg Lys Leu Leu Glu Gly Ser Arg
341                                          350
Phe Ala Val His His Glu Glu Glu Val Lys
351                                          360
Val Lys Asp Asp Glu Gly Ile Leu Arg Gln
361                                          370
Asp Arg Tyr Pro Leu Arg Thr Ser Pro Gln
371                                          380
Trp Leu Gly Pro Leu Val Ser Asp Leu Ile
381                                          390
His Ala His Ala Val Leu Thr Ile Glu Ala
391                                          400
Gly Gln Ser Thr Thr Asp Asn Pro Leu Ile
401                                          410
Asp Val Glu Asn Lys Thr Ser His His Gly
411                                          420
Gly Asn Phe Gln Ala Ala Ala Vla Ala Asn
421                                          430
Thr Met Glu Lys Thr Arg Leu Gly Leu Ala
431                                          440
Gln Ile Gly Lys Leu Asn Phe Thr Gln Leu
441                                          450
Thr Glu Met Leu Asn Ala Gly Met Asn Arg
451                                          460
Gly Leu pro Ser Cys Leu Ala Ala Glu Asp
461                                          470
Pro Ser Leu Ser Tyr His Cys Lys Gly Leu
471                                          480
Asp Ile Ala Ala Ala Tyr thr Ser Glu
481                                          490
Leu Gly his Leu Ala Asn Pro Val Thr Thr
401                                          500
His Val Gln Pro Ala Glu Met Ala Asn Gln
501                                          510
Ala Val Asn Ser Leu Ala Leu Ile Ser Ala
511                                          520
Arg Arg thr Thr Glu Ser Asn Asp Val Leu
521                                          530
Ser Leu Leu Leu Ala Thr His Leu Tyr Cys
531                                          540
Val Leu Gln Ala Ile Asp Leu Arg Ala Ile
541                                          550
Glu Phe Glu Phe Lys Lys Gln Phe Gly Pro
551                                          560
Ala Ile Val Ser Leu Ile Asp Gln His Phe
561                                          570
Gly Ser Ala Met Thr Gly Ser Asn Leu Arg
571                                          580
Asp Glu Leu Val Glu Lys Val Asn Lys Thr
581                                          590
Leu Ala Lys Arg Leu Glu Gln Thr Asn Ser
591                                          600
Tyr Asp leu Val Pro Arg Trp His Asp Ala
601                                          610
Phe Ser Phe Ala Ala Gly Thr Val Val Glu
611                                          620
Val Leu Ser Ser Thr Ser Leu Ser Leu Ala
```

```
                    -continued
621                                          630
Ala Val Asn Ala Trp Lys Val Ala Ala Ala
631                                          640
Glu Ser Ala Ile Ser Leu Thr Arg Gln Val
641                                          650
Arg Glu Thr Phe Trp Ser Ala Ala Ser Thr
651                                          660
Ser Ser Pro Ala Leu Ser Tyr Leu Ser Pro
661                                          670
Arg Thr Gln Ile Leu Tyr Ala Phe Val Arg
671                                          680
Glu Glu Leu Gly Val Lys Ala Arg Arg Gly
681                                          690
Asp Val phe Leu Gly Lys Gln Glu Val Thr
691                                          700
Ile Gly Ser Asn Val Ser Lys Ile Tyr Glu
701                                          710
Ala Ile Lys Ser Gly Arg Ile Asn Asn Val
711              716
Leu Leu Lys Met Leu Ala
```

2. The L-phenylalanine ammonia-lyase of claim 1, wherein the transformant is a recombinant microorganism FERM BP-1710 of *Escherichia coli*.

3. The L-phenylalanine ammonia-lyase of claim 1, wherein the transformant is a recombinant microorganism FERM BP-1712 of *Escherichia coli*.

4. The L-phenylalanine ammonia-lyase of claim 1, produced by a process comprising the steps of:

cultivating yeast Rhodosporidium toruloides under conditions to induce L-phenylalanine ammonialyase, harvesting the yeast cells, placing the harvested cells into liquid nitrogen to freeze the yeast cells, separating the fraction containing L-phenylalanine ammonialyase mRNA from the frozen yeast cells, forming a single strand cDNA from the mRNA with a reverse transcriptase, transforming the single strand cDNA into a double strand cDNA, introducing the double strand cDNA into a vector, transforming a host cell by the vector to make a cDNA library, cloning the cDNA coding for the L-phenylalanine ammonialyase structural gene from the library, preparing a hybrid plasmid using the cloned cDNA to make a transformed L-phenylalanine ammonialyase-producing cell, cultivating the L-phenylalanine ammonialyase-producing cell to produce L-phenylalanine ammonialyase, and recovering the L-phenylalanine ammonialyase so produced.

* * * * *